(12) United States Patent
Bengtsson et al.

(10) Patent No.: US 10,300,213 B2
(45) Date of Patent: May 28, 2019

(54) CARTRIDGE AND NEEDLE ASSEMBLY IN COMBINATION

(71) Applicant: Novo Nordisk A/S, Bagsvaerd (DK)

(72) Inventors: Henrik Bengtsson, Taastrup (DK); Emil Gram Spork, Copenhagen N (DK)

(73) Assignee: Novo Nordisk A/S, Bagsvaerd (DK)

( * ) Notice: Subject to any disclaimer, the term of this patent is extended or adjusted under 35 U.S.C. 154(b) by 299 days.

(21) Appl. No.: 15/116,378

(22) PCT Filed: Jan. 26, 2015

(86) PCT No.: PCT/EP2015/051494
§ 371 (c)(1),
(2) Date: Aug. 3, 2016

(87) PCT Pub. No.: WO2015/117854
PCT Pub. Date: Aug. 13, 2015

(65) Prior Publication Data
US 2017/0007775 A1    Jan. 12, 2017

(30) Foreign Application Priority Data
Feb. 6, 2014    (EP) .................................. 14154149

(51) Int. Cl.
*A61M 5/24* (2006.01)
*A61M 5/32* (2006.01)

(52) U.S. Cl.
CPC ............ *A61M 5/3202* (2013.01); *A61M 5/24* (2013.01); *A61M 5/3232* (2013.01); *A61M 2005/2403* (2013.01); *A61M 2005/2411* (2013.01); *A61M 2005/2474* (2013.01)

(58) Field of Classification Search
CPC ..... A61M 5/3202; A61M 5/24; A61M 5/3232
See application file for complete search history.

(56) References Cited

U.S. PATENT DOCUMENTS

| 4,392,859 | A | * | 7/1983 | Dent ..................... A61M 5/326 604/198 |
| 4,416,663 | A |   | 11/1983 | Hall |
| 4,775,376 | A | * | 10/1988 | Strung ................. A61M 5/001 604/122 |
| 6,126,646 | A |   | 10/2000 | Hansen et al. |

(Continued)

FOREIGN PATENT DOCUMENTS

| JP | H0751370 A | 2/1995 |
| WO | 2012025639 A1 | 3/2012 |
| WO | 2014064100 A1 | 5/2014 |

*Primary Examiner* — Rebecca E Eisenberg
*Assistant Examiner* — Tasnim Mehjabin Ahmed
(74) *Attorney, Agent, or Firm* — Wesley Nicolas

(57) ABSTRACT

The present invention relates to a combined cartridge and needle assembly (10, 15) for use in a re-useable injection device The cartridge (10) containing a pharmaceutical liquid drug and the needle assembly (15) with a needle cannula (25) is permanently attached to each other to form one single unit mountable in the re-usable injection device. The needle assembly (15) is preferably also provided with a spring operated telescopic shield (20) which carries a reservoir (40) containing a cleaning solvent for cleaning at least the distal tip (27) of the needle cannula (25) between injections.

7 Claims, 5 Drawing Sheets

(56) References Cited

U.S. PATENT DOCUMENTS

| | | | |
|---|---|---|---|
| 6,210,369 B1* | 4/2001 | Wilmot | A61M 5/2033 |
| | | | 604/157 |
| 2006/0129122 A1* | 6/2006 | Wyrick | A61M 5/2033 |
| | | | 604/506 |
| 2013/0324965 A1 | 12/2013 | Lawlis et al. | |
| 2016/0271319 A1* | 9/2016 | Bengtsson | A61M 5/2466 |

* cited by examiner

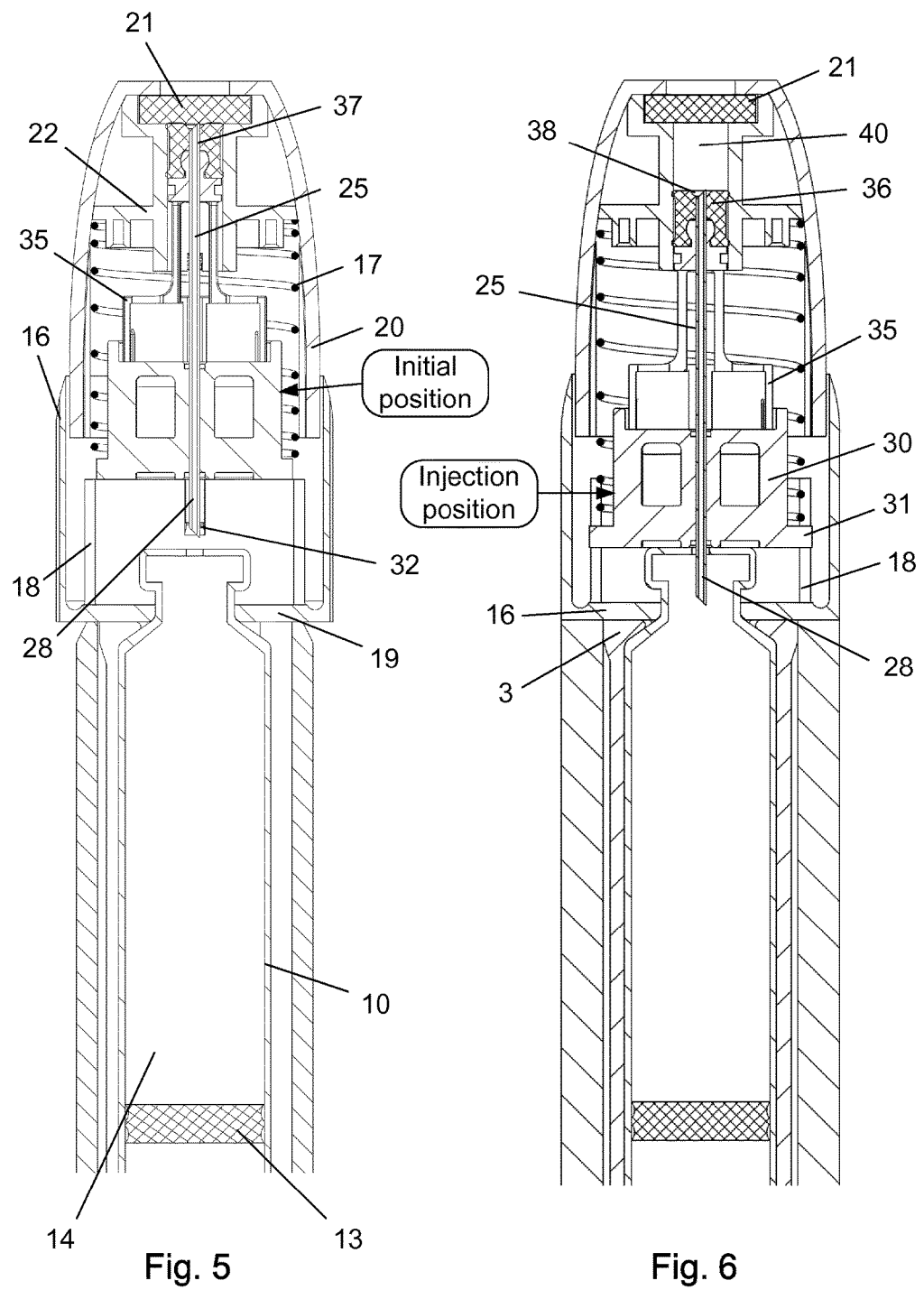

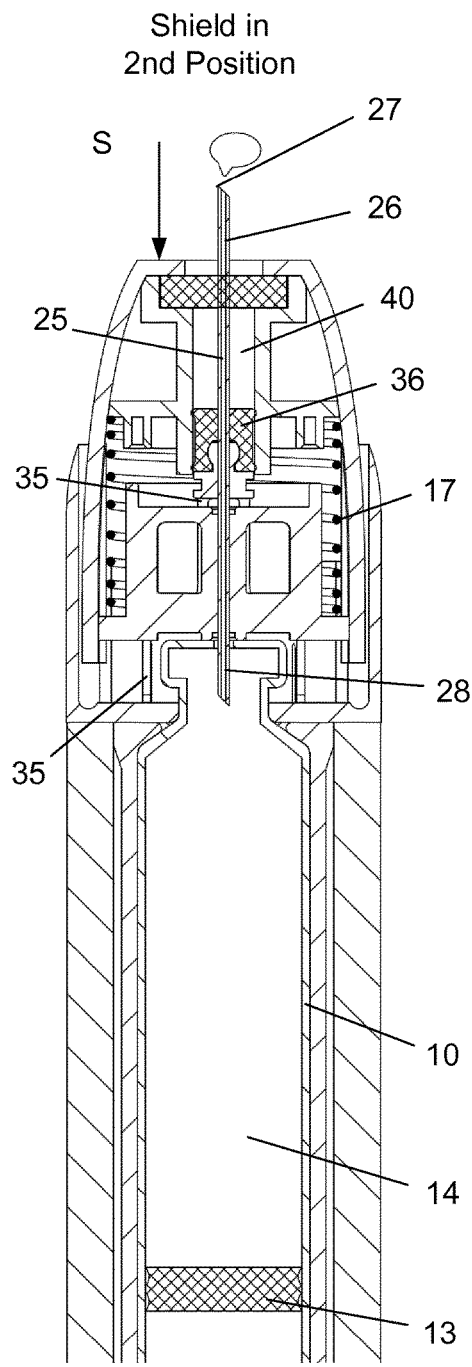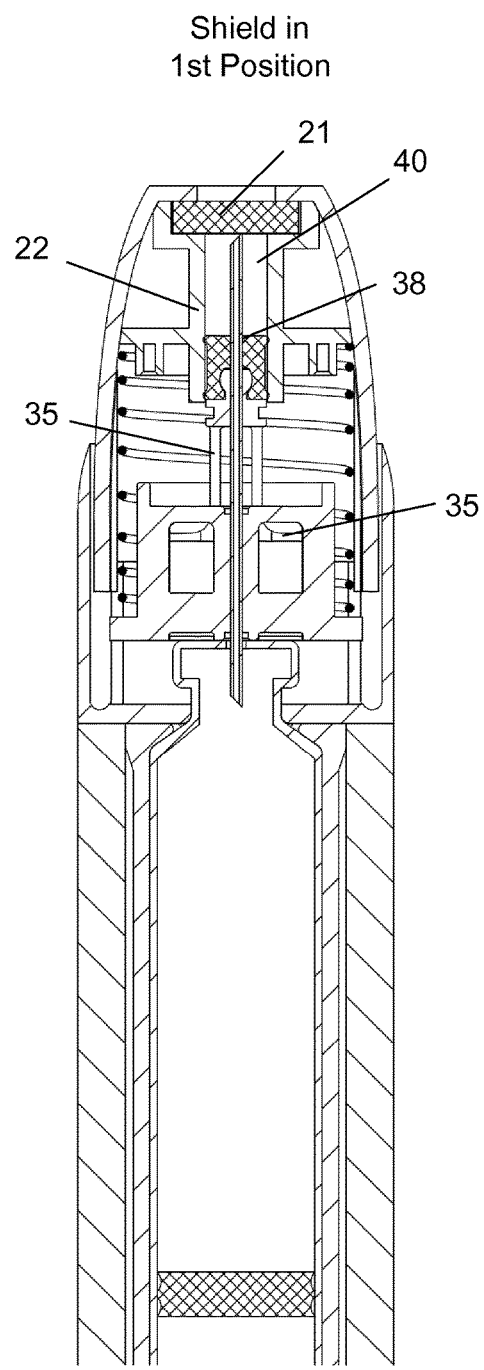
Fig. 7
Fig. 8

CARTRIDGE AND NEEDLE ASSEMBLY IN COMBINATION

CROSS-REFERENCE TO RELATED APPLICATIONS

This application is a 35 U.S.C. § 371 National Stage application of International Application PCT/EP2015/051494 (published as WO 2015/117854), filed Jan. 26, 2015, which claims priority to European Patent Application 14154149.0, filed Feb. 6, 2014; the contents of which are incorporated herein by reference.

THE TECHNICAL FIELD OF THE INVENTION

The invention relates to a cartridge and needle assembly in combination. The cartridge and the needle assembly are permanently attached such that the two parts together form one single unit which in all matters are handled as one unitary unit.

The unit thus comprising the cartridge and the needle assembly is configured for use with a durable injection device.

DESCRIPTION OF RELATED ART

U.S. Pat. No. 6,126,646 disclose a cartridge to which a plastic adapter top is permanently connected. The connection between the cartridge and the plastic adapter top falls under the definition of "permanent" given in this description as it requires the operation of tools if the plastic adapter top is to be removed and it would damage at least the metal cap of the cartridge should the plastic adapter top be successfully removed. The plastic adapter top is further provided with connection means located on an outer surface for removable connection of an exchangeable needle assembly.

WO 2014/064100 discloses a prefilled disposable injection device which in one embodiment carries a needle cannula permanently attached to the injection device such that the pre-filled injection device and the needle cannula operates as one single unit.

However when using a durable injection device i.e. an injection device which requires the user to exchange the cartridge, the user has to perform several operations. Whenever the cartridge is empty the user must remove the used cartridge and insert a new cartridge. This requires the user to also remove the needle assembly. Further, the user needs to replace the needle assembly between injections.

DESCRIPTION OF THE INVENTION

It is an object of the present invention to provide a more simple operation of the injection device.

It is a particular object to make it possible to avoid changing the injection needle between injections thereby decreasing the required handling steps.

The invention is defined in the attached claim 1 followed by a number of embodiments. The individual claims are explained in details in the following.

Accordingly, in one aspect of the present invention, the combined cartridge and needle assembly comprises:
a cartridge containing a pharmaceutical liquid drug and having a distal end closed by a pierceable membrane and a proximal end closed by a movable plunger, and wherein the volume between the membrane and the movable plunger contains the pharmaceutical liquid drug, and, a needle assembly.

The needle assembly is permanently attached to the cartridge to form one unitary unit and further comprises:
A housing structure holding a needle cannula having a distal end with a tip and an opposite proximal end, and
A telescopic needle shield which is axially movable relatively to the housing structure between a first extended position and a second retracted position and which needle shield is urged into the extended position by a resilient member such as a spring.

The telescopic shield further carries a reservoir containing a liquid preservative for cleaning at least the tip of the needle cannula between subsequent.

Since the cartridge and the needle assembly comprising both the housing structure (carrying the needle cannula), and the telescopic needle shield (carrying the cleaning reservoir), is formed as one unitary unit, the user is simply just required to exchange this unit once the cartridge is empty. No further actions are required and since the tip of the needle cannula is automatically cleaned between subsequent injections, no further exchange of the needle cannula is required. The operation of the re-useable injection is thus made very simple as it requires very little interaction with the user.

The liquid preservative used in the cleaning reservoir is preferably identical to the preservative contained in the pharmaceutical liquid drug contained in the cartridge. This is described in details in International Patent Application No.: PCT/EP2014/071746.

The cleaning reservoir is preferably the room established between a distal septum and a proximal septum.

In the first extended position of the telescopic shield, the tip of the needle cannula is located inside the reservoir and in the second retracted position, the tip of the needle cannula is located distal to the telescopic shield to perform an injection.

The needle cannula is preferably secured to a hub which hub form part of the housing structure but which is axial movable relatively to the housing structure from an initial position to an injection position by the force of the resilient element. When a user releases the hub e.g. by rotating the housing, the resilient element urges the hub axially into the injection position in which the proximal end of the needle cannula is in liquid contact with the liquid drug inside the cartridge.

Further, means such as an arm locks the hub to the housing first time the hub enters into the injection position. The hub is hereafter maintained in that locked position.

The resilient element is preferably provided between the telescopic shield and the hub urging the telescopic shield in the distal direction. Further, an auxiliary member carrying the proximal septum of the reservoir is connected to the hub such that the auxiliary member can slide axially in relation to the hub. The reservoir is formed between this proximal septum and a distal septum carried by the shield.

When the hub moves into the injection position, the auxiliary member follows the hub thus creating the cleaning reservoir. In the injection position, the hub locks to the housing structure while the auxiliary member remains axially slidable in relation to the hub.

Definitions

An "injection pen" is typically an injection apparatus having an oblong or elongated shape somewhat like a pen for writing. Although such pens usually have a tubular cross-section, they could easily have a different cross-section such as triangular, rectangular or square or any variation around these geometries.

The term "Needle Cannula" is used to describe the actual conduit performing the penetration of the skin during injection. A needle cannula is usually made from a metallic material such as e.g. stainless steel and connected to a hub to form a complete injection needle also often referred to as a "needle assembly". A needle cannula could however also be made from a polymeric material or a glass material. The hub also carries the connecting means for connecting the needle assembly to an injection apparatus and is usually moulded from a suitable thermoplastic material. The "connection means" could as examples be a luer coupling, a bayonet coupling, a threaded connection or any combination thereof e.g. a combination as described in EP 1,536,854.

The term "Needle unit" is used to describe one single needle assembly carried in a container. Such container usually has a closed distal end and an open proximal end which is sealed by a removable seal. The interior of such container is usually sterile such that the needle assembly is ready-to-use. Needle units specially designed for pen injections systems are defined in ISO standard No. 11608, part 2, and are often referred to as "pen needles". Pen needles have a front-end for penetrating into the user and a back-end for penetrating into the cartridge containing the drug.

As used herein, the term "drug" is meant to encompass any drug-containing flowable medicine capable of being passed through a delivery means such as a hollow needle in a controlled manner, such as a liquid, solution, gel or fine suspension. Representative drugs includes pharmaceuticals such as peptides, proteins (e.g. insulin, insulin analogues and C-peptide), and hormones, biologically derived or active agents, hormonal and gene based agents, nutritional formulas and other substances in both solid (dispensed) or liquid form.

"Cartridge" is the term used to describe the container containing the drug. Cartridges are usually made from glass but could also be moulded from any suitable polymer. A cartridge or ampoule is preferably sealed at one end by a pierceable membrane referred to as the "septum" which can be pierced e.g. by the non-patient end of a needle cannula. Such septum is usually self-sealing which means that the opening created during penetration seals automatically by the inherent resiliency once the needle cannula is removed from the septum. The opposite end is typically closed by a plunger or piston made from rubber or a suitable polymer. The plunger or piston can be slidable moved inside the cartridge. The space between the pierceable membrane and the movable plunger holds the drug which is pressed out as the plunger decreased the volume of the space holding the drug. However, any kind of container—rigid or flexible—can be used to contain the drug.

Since a cartridge usually has a narrower distal neck portion into which the plunger cannot be moved not all of the liquid drug contained inside the cartridge can actually be expelled. The term "initial quantum" or "substantially used" therefore refers to the injectable content contained in the cartridge and thus not necessarily to the entire content.

By the term "Pre-filled" injection device is meant an injection device in which the cartridge containing the liquid drug is permanently embedded in the injection device such that it cannot be removed without permanent destruction of the injection device. Once the pre-filled amount of liquid drug in the cartridge is used, the user normally discards the entire injection device. This is in opposition to a "Durable" injection device in which the user can himself change the cartridge containing the liquid drug whenever it is empty. Pre-filled injection devices are usually sold in packages containing more than one injection device whereas durable injection devices are usually sold one at a time. When using pre-filled injection devices an average user might require as many as 50 to 100 injection devices per year whereas when using durable injection devices one single injection device could last for several years, however, the average user would require 50 to 100 new cartridges per year.

Using the term "Automatic" in conjunction with injection device means that, the injection device is able to perform the injection without the user of the injection device delivering the force needed to expel the drug during dosing. The force is typically delivered—automatically—by an electric motor or by a spring drive. The spring for the spring drive is usually strained by the user during dose setting, however, such springs are usually prestrained in order to avoid problems of delivering very small doses. Alternatively, the spring can be fully preloaded by the manufacturer with a preload sufficient to empty the entire drug cartridge though a number of doses. Typically, the user activates a latch mechanism e.g. in the form of a button on, e.g. on the proximal end, of the injection device to release—fully or partially—the force accumulated in the spring when carrying out the injection.

The term "Permanently connected" as used in this description is intended to mean that the parts, which in this application is embodied as a cartridge and a needle assembly, requires the use of tools in order to be separated and should the parts be successfully separated it would permanently damage at least one of the parts thereby preventing re-use of either of the parts.

All references, including publications, patent applications, and patents, cited herein are incorporated by reference in their entirety and to the same extent as if each reference were individually and specifically indicated to be incorporated by reference and were set forth in its entirety herein.

All headings and sub-headings are used herein for convenience only and should not be constructed as limiting the invention in any way.

The use of any and all examples, or exemplary language (e.g. such as) provided herein, is intended merely to better illuminate the invention and does not pose a limitation on the scope of the invention unless otherwise claimed. No language in the specification should be construed as indicating any non-claimed element as essential to the practice of the invention.

The citation and incorporation of patent documents herein is done for convenience only and does not reflect any view of the validity, patentability, and/or enforceability of such patent documents.

This invention includes all modifications and equivalents of the subject matter recited in the claims appended hereto as permitted by applicable law.

BRIEF DESCRIPTION OF THE DRAWINGS

The invention will be explained more fully below in connection with a preferred embodiment and with reference to the drawings in which:

FIG. 5 shows the combined cartridge and needle assembly mounted on the reusable injection device with the hub in the initial position.

FIG. 6 shows the combined cartridge and needle assembly mounted on the reusable injection device with the hub in the injection position.

FIG. 7 shows the combined cartridge and needle assembly mounted on the reusable injection device with the shield in the second retracted position.

FIG. 8 shows the combined cartridge and needle assembly mounted on the reusable injection device with the shield in the first extended position.

The figures are schematic and simplified for clarity, and they just show details, which are essential to the understanding of the invention, while other details are left out. Throughout, the same reference numerals are used for identical or corresponding parts.

DETAILED DESCRIPTION OF EMBODIMENT

When in the following terms as "upper" and "lower", "right" and "left", "horizontal" and "vertical", "clockwise" and "counter clockwise" or similar relative expressions are used, these only refer to the appended figures and not to an actual situation of use. The shown figures are schematic representations for which reason the configuration of the different structures as well as there relative dimensions are intended to serve illustrative purposes only.

Figure 1:
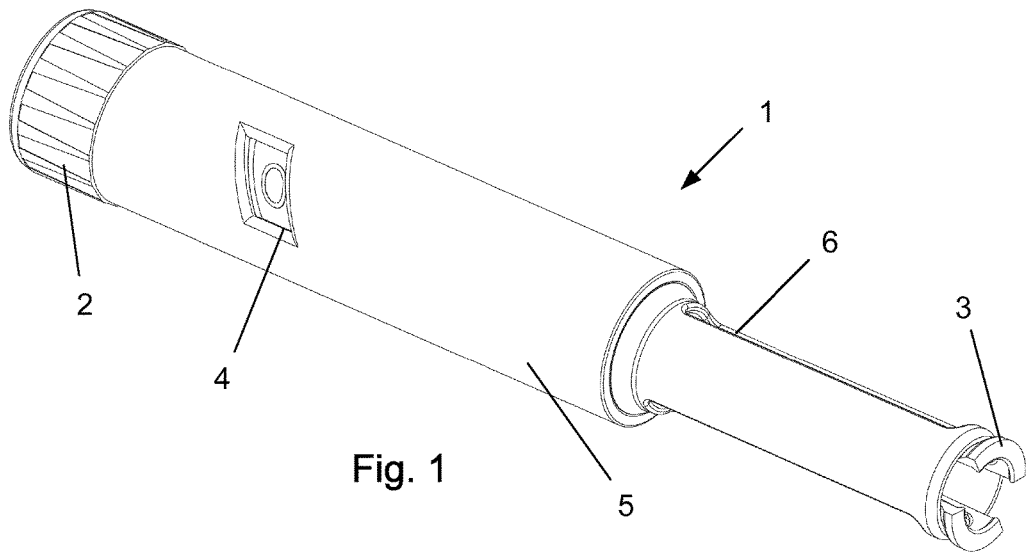
FIG. 1 shows a perspective view of a re-useable injection device.

In that context it may be convenient to define that the term "distal end" in the appended figures is meant to refer to the end of the injection device which usually carries the needle cannula whereas the term "proximal end" is meant to refer to the opposite end pointing away from the injection needle and carrying the injection button 2 as depicted in FIG. 1.

Figure 2:
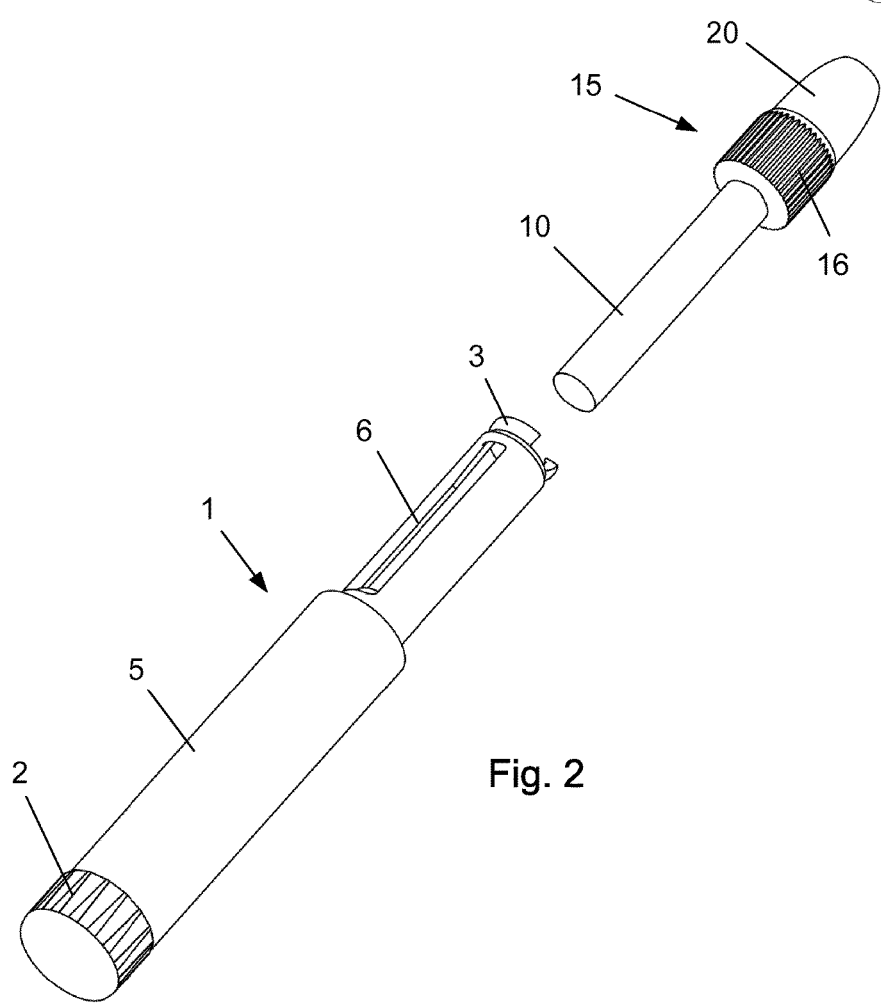
FIG. 2 shows the combined cartridge and needle assembly ready to be mounted into a re-useable injection device.

FIG. 1 discloses a perspective view of an injection device 1 and FIG. 2 discloses the combined cartridge 10 and needle assembly 15 ready to be connected to a durable injection device 1.

The durable injection device 1 is at the proximal end of the housing 5 provided with a dose setting button 2 which is rotated by the user in order to set a dose to be injected. Distally the injection device 1 is provided with a number of claws 3 which can be moved radially inwardly in order to secure the cartridge 10 to the injection device 1.

The housing 5 of the injection device 1 is further provided with at least two openings or windows 4, 6 in the sidewall. Through the proximal rectangular opening 4, the user is able to inspect the dose dial indicating the size of the dose being set, and through the distal longitudinal opening 6, the user can inspect the cartridge 10 and observe the content thereof once the cartridge 10 is mounted in the injection device 1.

Figure 3:
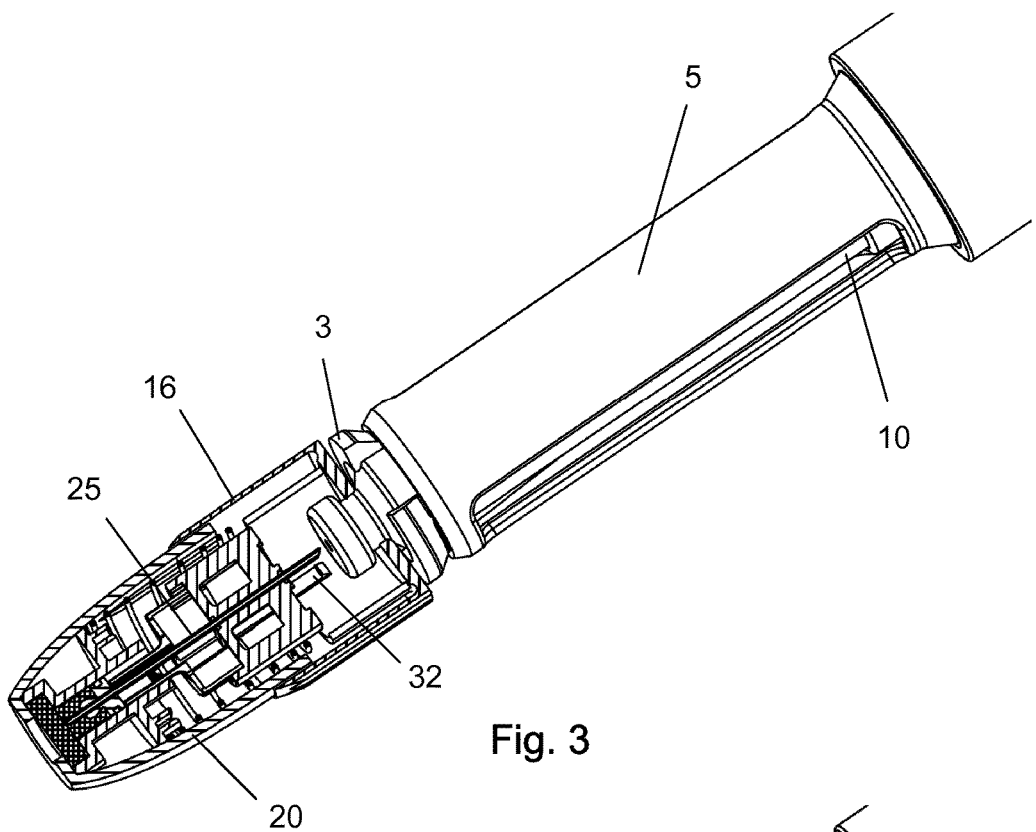
FIG. 3 shows the claws of a re-useable injection device engaging the combined cartridge and needle assembly.
Figure 4:
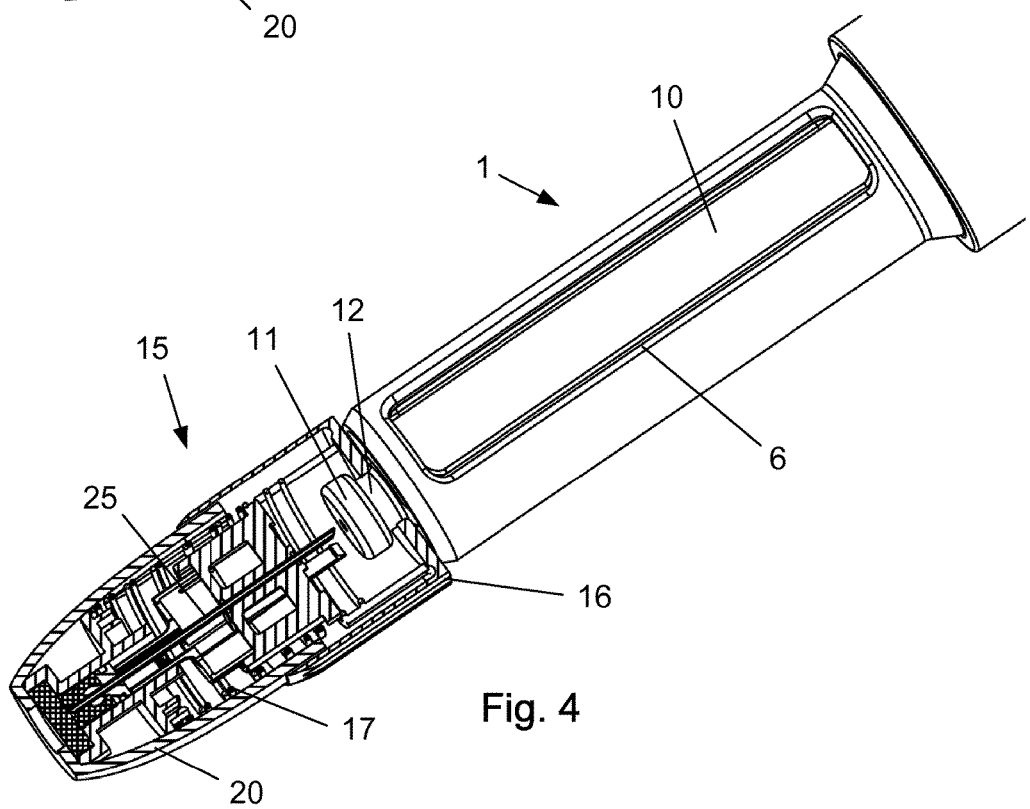
FIG. 4 shows the combined cartridge and needle assembly fully mounted to a reuseable injection device.

FIG. 3 and FIG. 4 depicts the combined cartridge 10 and needle assembly 15 being mounted in the injection device 1. The cartridge 10 is inserted from the distal end of the injection device 1 and the claws 3 are brought radially towards the centre-line by a not-shown mechanism.

The disclosed cartridge 10 is a standard glass cartridge 10 having a distal end which is closed by a pierceable septum which is secured to the cartridge 10 via a metal cap 11. Proximally to this metal cap 11, the cartridge 10 has a neck portion 12 which is grabbed by the claws 3 during mounting of the cartridge 10 in the injection device 1. As e.g. disclosed in FIG. 5, the proximal end of the cartridge 10 is sealed off by a movable plunger 13 and the liquid drug is contained in the chamber 14 provided between the septum and the plunger 13. The pierceable septum is preferably made from a material which can be penetrated by a needle cannula 25 thereby allowing the liquid drug to be pressed out from the chamber 14 by moving the movable plunger 13 distally.

Once the user tightens the claws 3 they move radially to grip the neck portion 12 of the cartridge 10 and proximally to pull the needle assembly 15 into contact with the injection device 1 as depicted in FIG. 4.

The needle assembly 15 when viewed from the outside as e.g. in FIG. 2 comprises besides the cartridge 10 also a housing structure 16 and a needle shield 20. The needle shield 20 is telescopic movable in a proximal direction to expose part of the needle cannula 25 during injection as will be explained later. The housing structure 16 of the needle assembly 15 is permanently secured behind the neck portion 12 of the cartridge 10 such that the needle assembly 15 cannot be removed from the cartridge 10. The cartridge 10 and the needle assembly 15 are thus permanently connected forming one single unitary unit.

The combined cartridge 10 and needle assembly 15 is further disclosed in the FIGS. 5 to 8 which depicts the combined unit mounted in a durable injection device 1.

FIG. 5 discloses the position once the claws 3 have been closed and the needle assembly 15 has been pulled into contact with the housing 5 of the injection device 1.

The housing 16 of the needle assembly 15 is permanently attached to the cartridge 10. This permanent attachment can be established in many different ways, but preferably, the needle assembly 15 has a flange 19 which grips behind the neck portion 12 of the cartridge 10.

The telescopic shield 20 is urged in the distal direction by a resilient element 17 which is encompassed between the shield 30 and a hub 30. The resilient element 17 is in this embodiment depicted as a traditional compression spring but could be embodied in numerous ways.

The hub 30, which forms part of the housing structure 16, further carries the needle cannula 25 which e.g. can be glued to the hub 30. The needle cannula 25 has a distal part 26 with a tip 27 for penetrating the skin of a user during operation, and a proximal part 28 for penetrating through the septum of the cartridge 10 such that a liquid flow can be established between the interior of the chamber 14 of the cartridge 10 and the user.

Distally the hub 30 supports an auxiliary member 35 which can slide axially in relation to the hub 30 and which auxiliary member 35 distally carries a proximal septum 36. The proximal septum 36 can be secured to the auxiliary member 35 in a number of different ways. Further, the proximal septum 36 has a channel 37 (FIG. 5) such that the proximal septum 36 can slide axially in relation the needle cannula 25. This channel 37 fits tight to the needle cannula 25 and ends distally in a conical opening 38 (FIG. 6) such that the tip 27 of the needle cannula 25 is not fully sealed even when the proximal septum 36 abuts the distal septum 21 carried by the shield 20 as e.g. depicted in FIG. 5.

The distal septum 21 is maintained in its position on the shield 20 by an insert 22 which is secured to the shield 20 e.g. by gluing or by welding. The insert 22 is also the seat for the resilient element 17.

Figure 9:
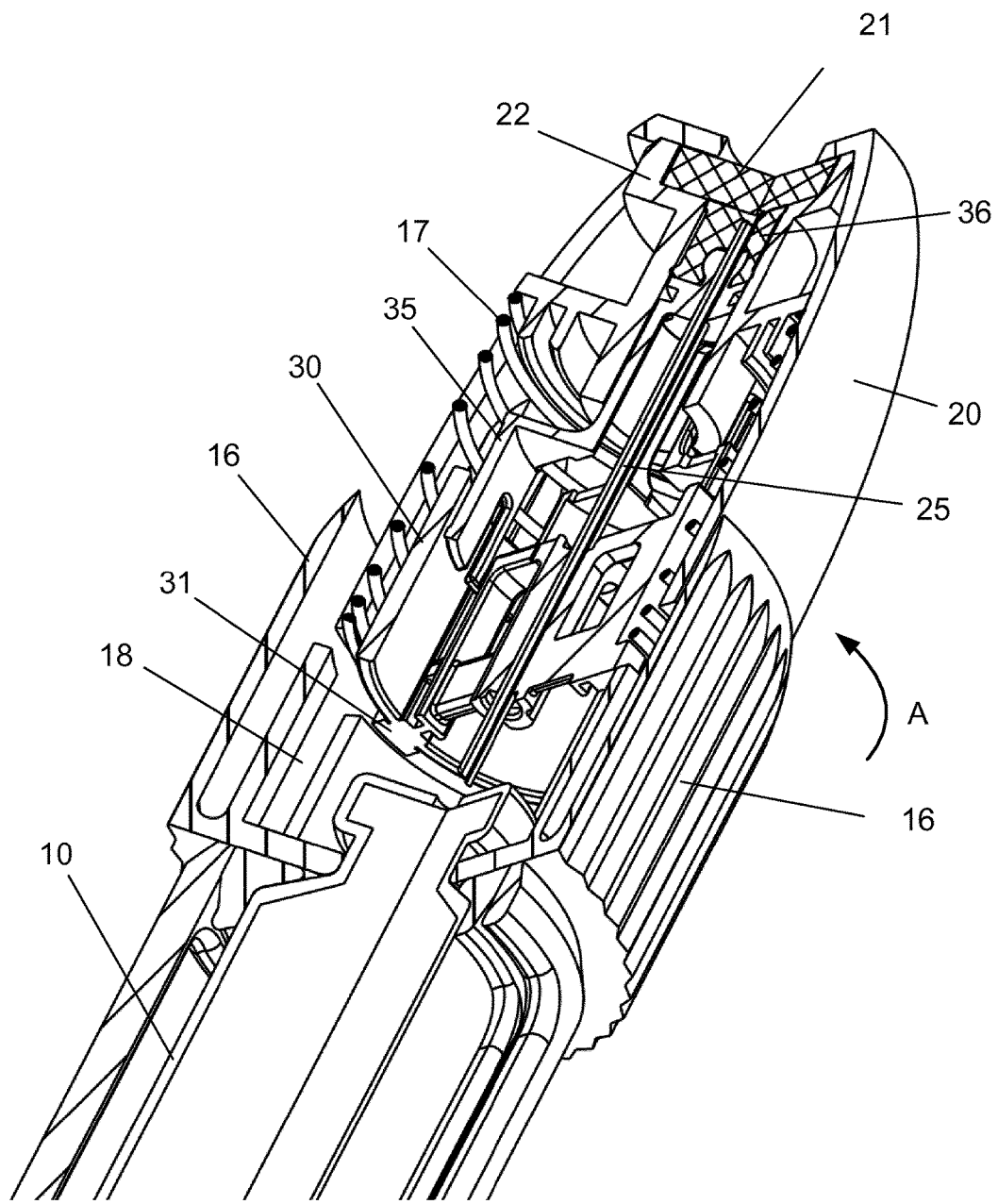
FIG. 9 shows a cut-up view of the combined cartridge and needle assembly mounted on the re-usable injection device as in FIG. 5 i.e. with the hub in the initial position.

Once the combined cartridge 10 and needle assembly 15 has been mounted in the injection device 1, the user rotates the housing structure 16 of the needle assembly 20 in the direction indicated by the arrow "A" in FIG. 9. This rotational movement moves a track 18 provided in the housing 16 into alignment with a protrusion 31 provided externally on the hub 30. Once the protrusion 31 is aligned with the track 18, the resilient element 17 shoots the hub 30 in the proximal direction to the injection position e.g. depicted in FIG. 6. This is further disclosed in FIG. 9, which is a cut-open view of the combined cartridge 10 and needle cannula 15 in the position depicted in FIG. 5 i.e. before the release of the resilient element 17.

Following this proximal movement of the hub 30, the proximal part 28 of the needle cannula 25 penetrates through the septum of the cartridge 10 as disclosed in FIG. 6. Further, the hub 30 pulls the auxiliary member 35 in a distal direction. Since the proximal septum 36 is attached to the auxiliary member 35 this also moves in the proximal direction such that a reservoir 40 is created between the distal septum 21 of the shield 20 and the proximal septum 36 of the auxiliary member 35.

As the hub 30, the auxiliary member 35 and the proximal septum 36 move from its start position (FIG. 5) to its proximal position (fog. 6) a vacuum is generated inside the reservoir 40. This vacuum automatically draws a quantum of liquid drug through the lumen of the needle cannula 25 from the chamber 14 of the cartridge 10 and into the reservoir 40. At the same time the proximal pointing arm 32 (FIG. 3) on the hub 30 locks to the housing 16 such that the hub 30 and the housing 16 hereafter are axial locked to each other. Once the reservoir 40 is filled as disclosed in FIG. 6, the injection device 1 is ready to perform a first injection. In this Ready-to-Inject position, the tip 27 of the needle cannula 25 is positioned in the conical opening 38 of the channel 37 which conical opening 38 is now a part of the reservoir 40.

When a user pushes the shield 20 against the surface of the skin as depicted in FIG. 7, the counter force (symbolized by the arrow "S") presses the shield 20 in a proximal direction against the force of the spring 17 and the tip 27 of the needle cannula 25 penetrates out through the distal septum 21 and into the skin of the user. When the tip 27 of the needle cannula 25 is in this position an injection can be performed. The injection is e.g. done manually by the user pressing an injection button back into the housing, or the injection can be performed automatic by the user pushing a button which either starts an electric motor to drive the injection or releases a spring which generates the force to drive the injection. Instead of the user activating a button, the injection can be triggered by the proximal movement of the shield 20, which is often referred to as shield-triggered injection.

When the shield 20 move proximal from the position in FIG. 6 to the position in FIG. 7, the liquid drug inside the reservoir 40 keeps the reservoir 40 at a constant volume and the auxiliary member 35 is forced to move with the shield 20. In that respect, the auxiliary member 35 is mounted inside the hub 30 such that it can slide axially in relation to the hub 30.

Once the desired quantum of liquid drug has been delivered through the lumen of the needle cannula 25, the tip 27 of the needle cannula 25 is removed from the skin of the user and the shield 20 is urged distally by the spring 17 as disclosed in FIG. 8.

In order to prevent the shield from continuing a distal movement non-shown stop protrusions can be provided between the shield 20 and the housing 16. In the position disclosed in FIG. 8, which is the position in which the tip 27 of the needle cannula 25 is maintained between injections, the tip 27 is located inside the reservoir 40 such that the preservatives in the liquid drug in the reservoir 40 keeps the tip 27 of needle cannula 25 clean between injections.

Further injections can now be performed as described in relation to FIG. 7 since the hub 30 is locked to the housing 16 via the arm 32. Once the chamber 14 of the cartridge 10 is empty, the combined cartridge 10 and needle assembly 15 can be replaced by a new unit.

Some preferred embodiments have been shown in the foregoing, but it should be stressed that the invention is not limited to these, but may be embodied in other ways within the subject matter defined in the following claims.

The invention claimed is:

1. A cartridge and needle assembly in combination for a re-useable injection device, comprising:
   a cartridge containing a pharmaceutical liquid drug and having a distal end closed by a pierceable membrane and a proximal end closed by a movable plunger, and
   a needle assembly comprising:
      a housing structure supporting a needle cannula having a distal end with a tip and a proximal end wherein the housing structure comprises a hub carrying the needle cannula and which hub is axial movable in the proximal direction relative to the housing structure from an initial position to an injection position, and
      a telescopic needle shield which is axially movable relatively to the housing structure between a first extended position and a second retracted position and which needle shield is urged into the first extended position by a resilient element,
         wherein the telescopic shield carries a reservoir containing a liquid preservative for cleaning at least the tip of the needle cannula between subsequent injections, wherein the reservoir comprises a distal septum and a proximal septum;
   wherein the needle assembly is permanently attached to the cartridge to form one unitary unit, and
   wherein at least the tip of the needle cannula in the first extended position of the telescopic needle shield is located inside the reservoir and wherein at least the tip of the needle cannula in the second retracted position of the telescopic needle shield is located distal to the telescopic needle shield to perform an injection.

2. A cartridge and needle assembly in combination according to claim 1, wherein the hub is axially movable from the initial position to the injection position by an axial force delivered by the resilient member.

3. A cartridge and needle assembly in combination according to claim 1, wherein the hub is locked to the housing structure in the injection position.

4. A cartridge and needle assembly in combination according to claim 3, wherein the hub is provided with a proximal extending arm which locks the hub to the housing in the injection position.

5. A cartridge and needle assembly in combination according to claim 1, wherein the resilient element is provided between the telescopic shield and the hub urging the telescopic shield in the distal direction.

6. A cartridge and needle assembly in combination according to claim 1, wherein the hub is connected to an auxiliary member which auxiliary member carries the proximal septum of the reservoir.

7. A cartridge and needle assembly in combination according to claim 6, wherein the reservoir is formed between the proximal septum carried by the auxiliary member and the distal septum carried by the shield.

* * * * *